United States Patent [19]
Callahan et al.

[11] Patent Number: 4,638,056
[45] Date of Patent: Jan. 20, 1987

[54] OPTHALMIC WAFER

[75] Inventors: Wayne B. Callahan, Milton; Harold O. Koch, Barboursville; Philip R. Palin; James R. Cook, both of Huntington, all of W. Va.

[73] Assignee: Cilco, Inc., Huntington, W. Va.

[21] Appl. No.: 528,857

[22] Filed: Sep. 2, 1983

Related U.S. Application Data

[63] Continuation-in-part of Ser. No. 516,341, Jul. 22, 1983, abandoned.

[51] Int. Cl.$^4$ .......................... A61F 2/16; C07H 5/04; C07H 5/10
[52] U.S. Cl. .................................... 536/54; 536/55.1; 536/118; 623/6
[58] Field of Search ....................... 3/13; 536/55.1, 54, 536/118

[56] References Cited

U.S. PATENT DOCUMENTS 4,141,973  2/1979  Balazs ................................. 536/55.1
4,517,295  5/1985  Bracke et al. ....................... 536/55.1
4,534,069  8/1985  Kelman ................................... 623/6

OTHER PUBLICATIONS

Healon (Sodium Hyaluronate) Product Monograph, (Pharmacia Laboratories).
Chondron Product Monograph (Kaken Pharmaceutial Co., Ltd.).
Drugs in Japan, Ethical Drug Edition, p. 216, (Japan Pharmaceutical Information Center 1975) (with English Translation).

Primary Examiner—Mark L. Bell
Attorney, Agent, or Firm—Pravel, Gambrell, Hewitt & Kimball

[57] ABSTRACT

Damage to endothelial and epithelial cells subject to trauma can be substantially reduced by using a wafer of a viscoelastic material. This method is particularly useful when applied prior to ophthalic surgery, particularly intraocular lens implantation surgery. Lens implantation is facilitated by the compression of lens haptics by this delivery system.

8 Claims, 4 Drawing Figures

OPTHALMIC WAFER

CROSS-REFERENCE TO RELATED APPLICATION

This is a continuation-in-part of our prior application, Ser. No. 516,341, filed July 22, 1983, now abandoned, the entire specification of which is incorporated herein by reference.

FIELD OF THE INVENTION

The present invention relates to a method of protecting both human and animal endothelial and epithelial cells which are subject to exposure to trauma. More particularly, this invention concerns protecting endothelial and epithelial cells in anticipation of surgical trauma using a wafer of a visco-elastic material. The present invention also relates to the wafer's ability to compress the lens haptics providing a more compact implantation system.

BACKGROUND OF THE INVENTION

The invention relates to a product for protecting both human and animal endothelial and epithelial cells which are subject to exposure, and to products of a visco-elastic material for protecting endothelial and epithelial cells in anticipation of surgical trauma.

Since human corneal endothelial cells are not known to reproduce, it is of vital importance to protect endothelia to prevent cell damage prior to subjection to anticipated trauma, such as surgery. Recent advances in opthalmic surgery have increased the need to protect corneal endothelial cells which may be subject to irreversible destruction during such surgery. Of particular significance is the need to protect corneal endothelial cells during intra-ocular lens (IOL) implantation, corneal transportation, and other intraocular surgical operations. Previous work in this field has been directed to protecting corneas with both non-biological and biological polymers.

Macromolecules heretofore employed in the protection of corneas include viscoelastic materials such as chondroitin sulfate solution for the protection of corneal surface tissue, described in a "CHONDRON" product monograph, Kaken Pharmaceutical Company, Ltd., Tokyo, Japan, 1981. The use of sodium hyaluronate as an aid in ophthalmic surgery is described in a "HEALON" product monograph, Pharmacia Laboratories, Piscataway, N.J., 1981.

The employment of the aforesaid macromolecules has not met with complete satisfaction due to insufficient cell protection, i.e., lack of sufficient viscoelastic material to prevent IOL-endothelial contact and consequent significant corneal endothelial cell damage.

In view of the above, it would be advantageous to prepare a solid product of viscoelastic material, which could be used in surgery to insure separation of an intraocular lens from corneal endothelial cells and thereby prevent significant corneal endothelial cell damage, as well as provide a lens delivery system that eases the physical aspects of lens implantation.

SUMMARY OF THE INVENTION

It has now been discovered that one or more viscoelastic materials such as chondroitin sulfate or sodium hyaluronate may be formed in a wafer, designed to hold an intraocular lens and offering superior protection to corneal surface cells during intraocular lens implantation. The viscoelastic wafers of the present invention can be molded or cast through a curing process. The cured viscoelastic wafers of the present invention maintain a solid form until exposed to moisture.

BRIEF DESCRIPTION OF THE DRAWINGS

The drawings illustrate a typical wafer of viscoelastic material in accordance with the present invention. The water is characterized by two overhangs (10, 12) designed to hold an intraocular lens (not shown), and at least provide one grip area for the surgeon's forceps.

DETAILED DESCRIPTION OF THE INVENTION

Figure 1:
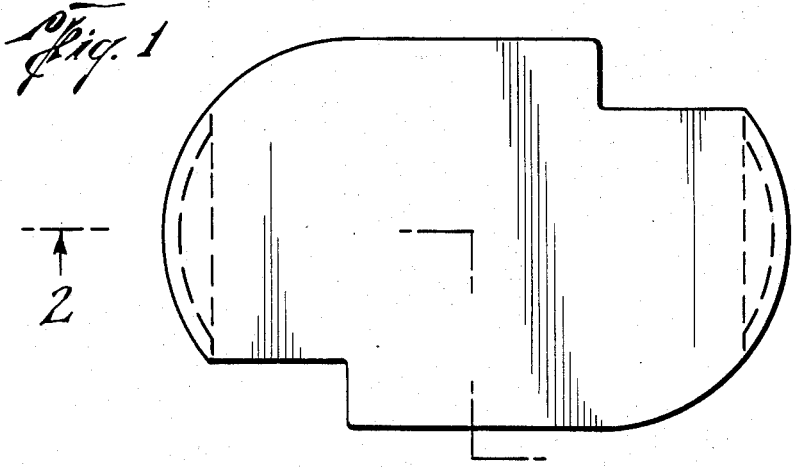
Figure 2:
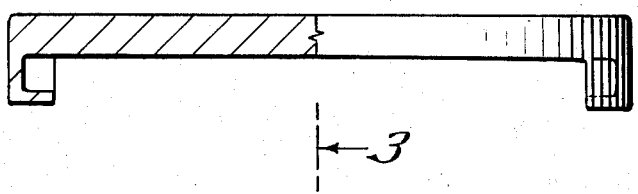
Figure 3:
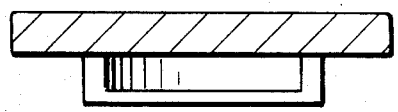
Figure 4:
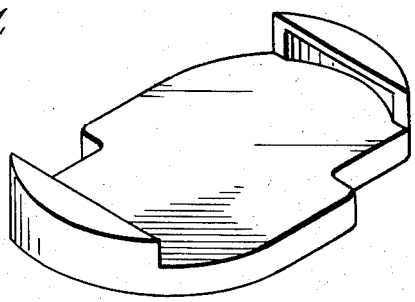

The present invention provides a solid product manufactured by molding or casting a viscoelastic material into a wafer that, when dried under controlled conditions is: (1) the appropriate size for insertion into either the anterior or posterior chamber of a human or animal eye, as required (approximately 10 mm×7 mm), (2) designed to collapse the loops of a posterior chamber lens to a size small enough to allow insertion through the iris into the posterior chamber without damaging the iris, and (3) designed to dissolve within about 0.25 to about 10.0 minutes releasing the loops of a posterior chamber lens or the feet of an anterior chamber lens. The viscoelastic material is preferably chondroitin sulfate, and most preferably sodium chondroitin sulfate. Other viscoelastic materials such as sodium hyaluronate may also be used, and mixtures of chondroitin sulfate and hyaluronate are also contemplated. In addition to sodium salts, potassium, calcium and magnesium salts are also contemplated in the practice of the invention. Sodium hyaluronate has the disadvantage of causing intraocular pressure postoperatively and is consequently recommended for removal from the anterior chamber prior to closing the corneal incision. The preferred viscoelastic material, sodium chondroitin sulfate, has been shown to offer excellent protection for corneal endothelium and monkey corneal endothelium during cataract extraction and intraocular lens implantation without intraocular pressure elevation. It has been found that intraocular pressure is somewhat reduced the first day after surgery (consistent with usual postoperative hypotony) with a return to normal levels the second or third day after surgery.

Chondroitin sulfate itself appears to be broken down as a part of the healing process. The sulfur atom of chondroitin sulfate has been radioactively traced and found to be incorporated into the healing tissue. Chondroitin sulfate apparently diminishes tissue rejection during tissue implants, acting in an active role that serves various surgical procedures including those of ophthalmology.

The present invention includes the utilization of a wafer of viscoelastic material, preferably chondroitin sulfate, as a lens delivery system as well as a protective agent prior to surgery to minimize or eliminate cell damage. Chondroitin sulfate may also be administered during surgery to make up any deletion occurring during surgical procedures such as vitreous loss. The use of chondroitin sulfate after surgery shows a potential for effectiveness in promoting the healing process.

It is known, for example, that prior to the present invention cataract surgery involving intraocular lens implantation, resulted in approximately 15% to approximately 75% loss of corneal endothelial cells depending on the surgical trauma. A great deal of cell loss results in undue cornea swelling. The viscoelastic wafers of the present invention provide an effective manner to significantly reduce such cell loss and simultaneously reduce or eliminate cornea swelling, without the occurrence of undue side effects.

Intraocular lenses for surgical insertions come in various types and shapes. There are basically two types of intraocular lenses. One type is an injection molded intraocular lens and the other is a lathe cut intraocular lens. Of the lathe cut type, many lens manufacturers use a methylmethacrylate known as PERSPEX CQ which is a medical grade methylmethacrylate produced by Imperial Chemical Industries, Ltd., of the United Kingdom. The injection molded lens types are usually made from the methylmethacrylate manufactured in the United States by the Rohm & Haas Company. The viscoelastic wafers of the present invention effectively guard against damage attributable to the intraocular lens-endothelial cell contact, and the degree of protection is not dependent upon particular shape or composition of the intraocular lens.

The viscoelastic wafers of the present invention are designed to be used with various types of either anterior chamber intraocular lenses or posterior chamber intraocular lenses. Examples of the surgical use of viscoelastic wafers of the present invention are set forth below.

Anterior Chamber Intraocular Lens

The anterior chamber intraocular lens will be slid into a viscoelastic wafer of the present invention. Thereafter the surgeon will grasp the designated end of the viscoelastic wafer, which now holds the lens with its anterior side covered, with forceps. This wafer/lens combination will then be inserted into the anterior chamber, after cataract extraction. The wafer will be positioned in the same manner as described for anterior chamber lens surgical procedures. Upon dissolution of the wafer, the surgeon can perform any minor adjustments necessary for final placement of the lens. In dissolving, the viscoelastic material will act as a viscoelastic agent in protecting the intraocular tissues.

Posterior Chamber Intraocular Lens

The posterior chamber lens will be inserted into the wafer, thereby compressing the posterior chamber lens loops to a designated size. This will be accomplished immediately prior to lens implantation. The surgeon will then grasp the designated end of the wafer, which now holds the lens with its anterior side covered and insert it through the corneal incision, through the iris, and into the posterior chamber. The wafer will be of such dimension that manual dilation of the iris should not be necessary to achieve insertion. After the wafer dissolves, usually within 3 minutes, the loops of the posterior lens will expand and open to their full dimension. This will provide centration and placement of the lens as described in currently accepted surgical protocol. The surgeon may, at this time, effect any minor adjustments in placement as may be necessary. The dissolving viscoelastic material will also act as a viscoelastic agent, and provide protection of intraocular tissues.

WAFER PREPARATION

The wafers of the present invention may be prepared by molding. The mold is designed with a gripping area for a pair of forceps. Because of the intended surgical use of the wafers of the present invention, described above, it is preferred that the wafers are characterized by a dissolution time of 30 to 60 seconds. This is, of course, an important advantage of the wafers of the present invention. To avoid sharp corners, the overhangs (10,12) are rounded as shown in the drawing.

It has been found that the wafers of the present invention cure best when the mold is left at ambient temperature (about 20° C.) to cure by natural evaporation. This method requires approximately 20 hours. Attempts to accelerate curing by raising the curing temperature to greater than about 30° C. causes air bubbles, brittleness, dimensional variation, and incomplete wafers.

As described above, the wafers of the present invention are preferably formed from sodium chondroitin sulfate. It is preferred that a solution of about 20 percent by weight sodium chondroitin sulfate be used to make the wafers of the present invention. It has been found that if the sodium chondroitin sulfate concentration is about 10 percent by weight or less, then the surface and overhangs of the wafers are not well-formed. It has also been found that if the concentration of sodium chondroitin sulfate is greater than about 40 percent by weight, the overhangs become bulky and a lens cannot be properly placed in the resulting wafer. It is therefore important that the solution of viscoelastic material used to prepare the wafers of the present invention be of a suitable concentration, so that the surface and overhangs of the resulting wafers are well-formed, but not too heavy or bulky. As suitable concentrations for sodium chondroitin sulfate have been described, those skilled in the art will readily be able to determine suitable concentrations for other viscoelastic materials.

Finally, an attempt was made to prepare wafers by freeze-drying. It was found that this method of curing was too quick, not allowing the solution from the center of the mold to cure. Instead of a normal wafer being formed, it was found that small, white, pill-shaped bowls that resembled an aspirin tablet were formed.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all the features which would be considered as equivalents thereof by those skilled in the art to which this invention pertains.

What is claimed is:

1. A wafer of viscoelastic material adapted to hold an intraocular lens, wherein said viscoelastic material is chondroitin sulfate or a mixture of chondroitin sulfate and a hyaluronate.

2. The wafer set forth in claim 1, wherein said viscoelastic material is chondroitin sulfate.

3. The wafer set forth in claim 2, wherein said viscoelastic material is sodium chondroitin sulfate.

4. The wafer set forth in claim 1, wherein said viscoelastic material is a mixture of chondroitin sulfate and a hyaluronate.

5. The wafer set forth in claim 4, wherein said viscoelastic material is a mixture of sodium chondroitin sulfate and sodium hyaluronate.

6. A process of preparing a wafer of viscoelastic material selected from the group consisting of chondroitin sulfate and a mixture of chondroitin sulfate and a hyaluronate, adapted to hold an intraocular lens comprising molding a solution of said viscoelastic material, and curing said molded material to produce a solid wafer.

7. The process set forth in claim 6, wherein said curing is by evaporation at ambient temperature.

8. The process set forth in claim 6, wherein said curing step is by evaporation at ambient temperature under laminar air flow.

* * * * *